(12) United States Patent
Shih

(10) Patent No.: US 9,759,412 B2
(45) Date of Patent: Sep. 12, 2017

(54) ILLUMINATION TOOL

(71) Applicant: Leo Shih, Taichung (TW)

(72) Inventor: Leo Shih, Taichung (TW)

( * ) Notice: Subject to any disclaimer, the term of this patent is extended or adjusted under 35 U.S.C. 154(b) by 51 days.

(21) Appl. No.: 14/930,686

(22) Filed: Nov. 3, 2015

(65) Prior Publication Data

US 2017/0122548 A1   May 4, 2017

(51) Int. Cl.
*F21V 21/22* (2006.01)
*F21V 33/00* (2006.01)
*G01N 21/88* (2006.01)
*F21L 4/00* (2006.01)

(52) U.S. Cl.
CPC ......... *F21V 21/22* (2013.01); *G01N 21/8806* (2013.01); *F21L 4/00* (2013.01); *F21V 33/0084* (2013.01)

(58) Field of Classification Search
CPC .. F21V 33/0084; F21V 21/22; F21V 21/0965; F21V 21/0885; F21V 21/096; F21V 21/28; F21V 33/008; A61B 1/247
USPC ....... 362/139, 138, 119, 198, 572, 120, 573; 433/29
See application file for complete search history.

(56) References Cited

U.S. PATENT DOCUMENTS

| | | | |
|---|---|---|---|
| 1,596,328 A * | 8/1926 | Wilt | A61B 1/24 359/726 |
| 3,597,051 A * | 8/1971 | Copeland | A61B 3/1208 351/218 |
| 6,702,577 B2 * | 3/2004 | Wong | A61B 1/0669 433/30 |
| 7,510,295 B2 | 3/2009 | Shih | |
| 7,690,807 B2 * | 4/2010 | Verderber | A61B 1/247 362/120 |
| 7,954,972 B2 | 6/2011 | Coleman et al. | |
| 8,172,571 B2 * | 5/2012 | Watson | A61B 1/253 433/31 |
| 8,746,918 B1 | 6/2014 | Rubino | |
| 2005/0201085 A1 * | 9/2005 | Aikawa | F21L 4/045 362/198 |

* cited by examiner

*Primary Examiner* — Anh Mai
*Assistant Examiner* — Arman B Fallahkhair
(74) *Attorney, Agent, or Firm* — Alan D. Kamrath; Kamrath IP Lawfirm, P.A.

(57) ABSTRACT

An illumination tool contains: a body, an extension assembly, and a mirror assembly. The body includes an accommodation mount having a light emitting element which face a first direction, and the body also includes a magnetic sleeve. The extension assembly couples with the body, and between the extension assembly and the body is defined a rotation structure. The mirror assembly includes a fitting portion, a holder and a first mirror which face a second direction. The holder has an L-shaped channel, and a first end of the channel corresponds to the accommodation mount. The lights illuminate into the channel from the first direction, and a second end of the channel curvedly extends to the second direction. The channel has a second mirror for reflecting the lights out of the second end of the channel in the second direction from the light emitting element in the first direction.

8 Claims, 10 Drawing Sheets

ILLUMINATION TOOL

FIELD OF THE INVENTION

The present invention relates to an illumination tool which illuminates a target object and magnetically attracts a metal object.

BACKGROUND OF THE INVENTION

Referring to FIG. 1, a multi-function penlight structure is disclosed in U.S. Pat. No. 7,510,295 and contains: a body 10, an accommodation mount 11 disposed on a front end of the body 10, a magnetic sleeve 12 mounted on a front edge of the accommodation mount 11 to magnetically attract a metal object, a hollow grip 13 in which an expandable stem 14 is fixed, and a flexible extension 15 connected with a front end of the expendable stern 14 and a rear end of the body 10. Thereby, the expandable stem 14 is extendable, and the flexible extension 15 is bendable. In operation, the expandable stem 14 is extended so that the body 10 moves forward, and the magnetic sleeve 12 magnetically attracts the metal object. In addition, the flexible extension 15 is bent so that the accommodation mount 11 of the body 10 faces the metal object, and the magnetic sleeve 12 of the accommodation mount 11 magnetically attracts the metal object. However, when desiring to view a target object in a limited space, the target object is stopped by the body 10.

As shown in FIG. 2, a multi-function telescopic flashlight is disclosed in U.S. Pat. No. 8,746,918 and contains a body 20. The body 20 includes: an accommodation mount 21 disposed on a front end thereof and facing a first direction, a magnetic sleeve 22 connected with a front edge of the accommodation mount 21 to magnetically attract a metal object, a hollow grip 23 in which an expandable stern 24 is mounted, and a flexible extension 25 connected with a front end of the expandable stern 24 and a rear end of the body 20. The expendable stem 24 extends outwardly, and the flexible extension 25 is bendable. The body 20 further includes a mirror assembly 26. The mirror assembly 26 has a fitting loop 261 with an opening to fit with the body 20, and the fitting loop 261 has a metal ring fixed therein, so that the magnetic sleeve 22 of the body 20 magnetically attracts the metal ring. Hence, the fitting loop 261 is mounted on the front end of the body 20. The fitting loop 261 has a connection shaft 262 disposed on an eccentric position thereof and has a rotating element 263 coupling with a front end of the connection shaft 262 and facing a mirror assembly 264 in a second direction, such that the mirror assembly 264 is adjustably moved to a desired angle by using the rotating element 263. Accordingly, when a target object is shielded, the flexible extension 25 is bent, so that the accommodation mount 21 and the mirror assembly 264 face the target object. Since the accommodation mount 21 illuminates lights to the first direction, and since the mirror assembly 264 faces the second direction, the mirror assembly 264 is adjustably moved toward a suitable position relative to the accommodation mount 21 by ways of the rotating element 263. The lights illuminate the mirror assembly 264 from the body 20, and the mirror assembly 264 reflects the lights to the target object, thus viewing the target object by way of the mirror assembly 264. Nevertheless, the multi-function telescopic flashlight has defects as follows:

1. The mirror assembly 264 is adjustably moved by using the rotating element 263 to reflect the lights toward the target object from the accommodation mount 21. Therefore, the lights from the body 20 intersect the mirror assembly 264 in the first direction, and the body 20 shields a part of the mirror assembly 264.

2. To intersect the lights from the body 20 with the mirror assembly 264 in the first direction to reflect the lights from the body 20 and to illumine the target object, the rotating element 263 is configured between the mirror assembly 264 and the body 20, thus increasing production cost of the multi-function telescopic flashlight.

As illustrated in FIG. 3, a light attachment 30 for an inspection tool is disclosed in U.S. Pat. No. 7,954,972 and contains a body 31. The body 31 includes: a mirror assembly 32 disposed on a side surface thereof and facing a second direction, and an accommodation mount 311 arranged on a peripheral side of the body 31 to house a light emitting element 33. The accommodation mount 311 has a rotating element 34 connecting with a shaft 35 which faces a first direction, such that the mirror assembly 32 and the light emitting element 33 are extendable and bendable. When desiring to view a target object in a limited space, the mirror assembly 32 and the light emitting element 33 of the body 31 are rotated by the rotating element 34 to shrink an obstruction and to ensure the mirror assembly 32 and the light emitting element 33 face the target object. Hence, the light emitting element 33 illuminates the target object, and the target object is visible by using the mirror assembly 32. However, the light emitting element 33 is housed in the accommodation mount 311 of the body 31, so the mirror assembly 32 cannot be removed solely, and the light attachment cannot be applied to pick other objects up.

The present invention has arisen to mitigate and/or obviate the afore-described disadvantages.

SUMMARY OF THE INVENTION

The primary objective of the present invention is to provide an illumination tool which magnetically attracts a metal object by using a magnetic sleeve.

A further objective of the present invention is to provide an illumination tool which illuminates lights to a target object by ways of a mirror assembly, thus viewing the target object clearly.

Another objective of the present invention is to provide an illumination tool which is manufactured easily, and a body of the illumination tool does not shield a first mirror of the mirror assembly to distinguish the target object clearly.

To obtain the above-mentioned objectives, an illumination tool provided by the present invention contains: a body, an extension assembly, and a mirror assembly.

The body includes an accommodation mount disposed on a front end thereof, and the accommodation mount has a light emitting element housed therein and facing first direction. The body also includes a magnetic sleeve.

The extension assembly couples with a rear end of the body, and between the extension assembly and the body is defined a rotation structure.

The mirror assembly includes a holder facing a second direction, a first mirror mounted on a first side surface of the holder and facing the second direction, and a fitting portion arranged on a second side surface of the holder and facing the first direction to fit with the body.

The holder has an L-shaped channel defined therein. A first end of the channel corresponds to the accommodation mount of the body, such that lights illuminate into the channel from the first direction, a second end of the channel curvedly extends to the second direction, and the channel has a second mirror fixed on a bending portion thereof to reflect the lights out of the second end of the channel in the second direction from the light emitting element in the first direction.

DETAILED DESCRIPTION OF THE PREFERRED EMBODIMENTS

Figure 1:
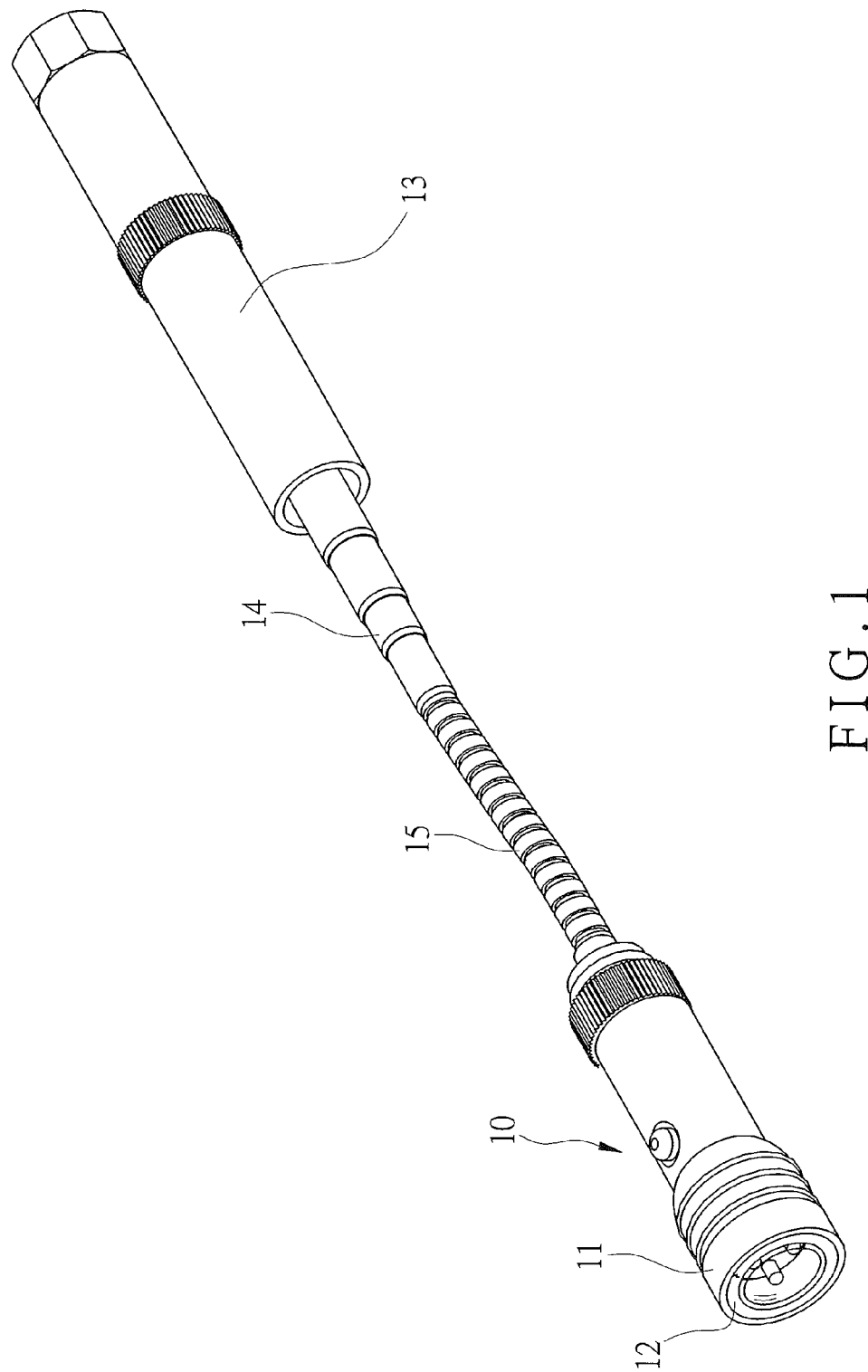
FIG. 1 is a perspective view of a multi-function penlight structure disclosed in U.S. Pat. No. 7,510,295.
Figure 2:
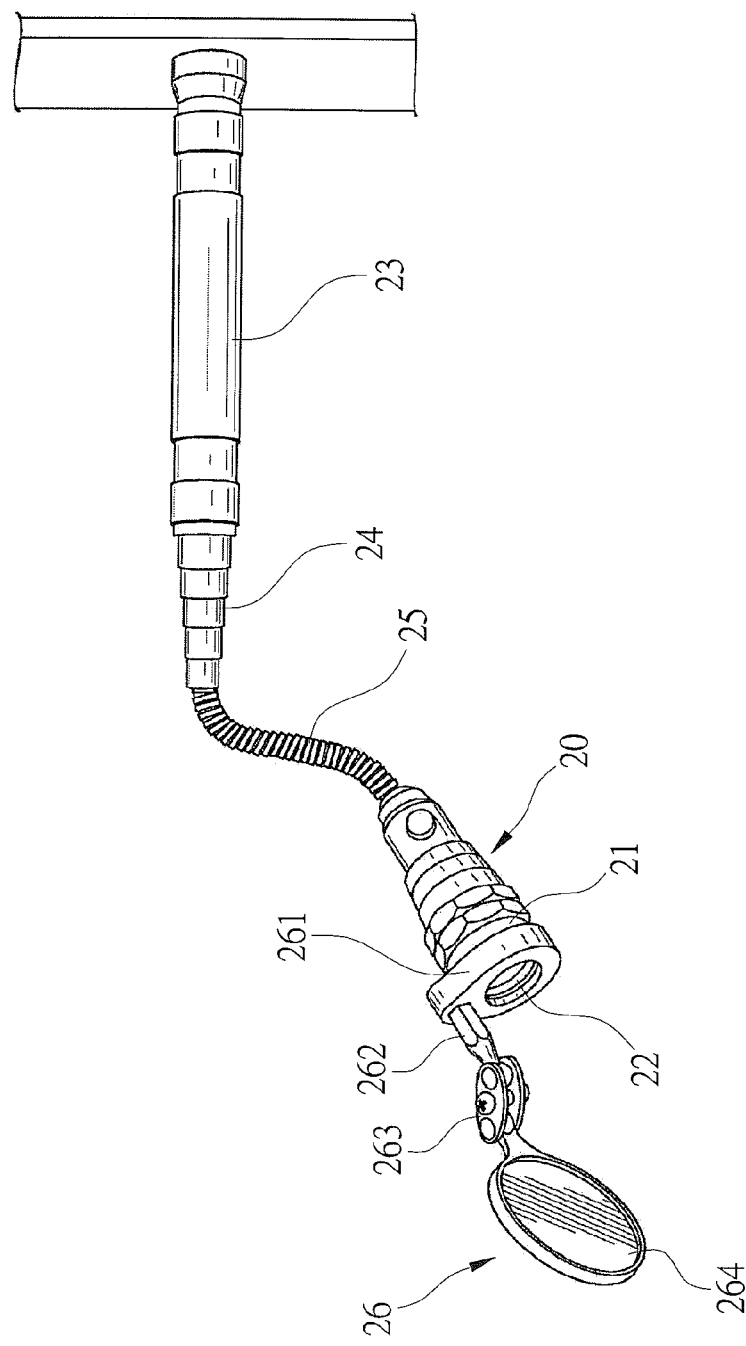
FIG. 2 is a perspective view of a multi-function telescopic flashlight in U.S. Pat. No. 8,746,918.
Figure 3:
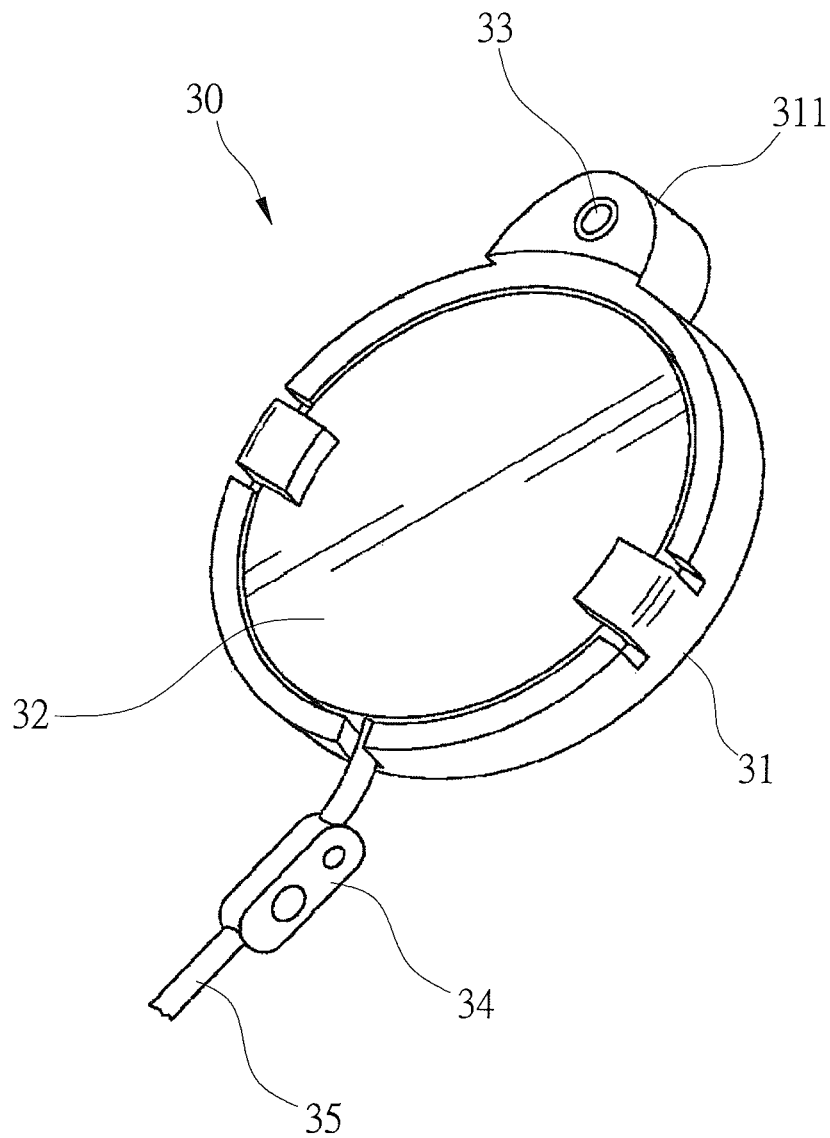
FIG. 3 is a perspective view of a light attachment for an inspection tool disclosed in U.S. Pat. No. 7,954,972.
Figure 4:
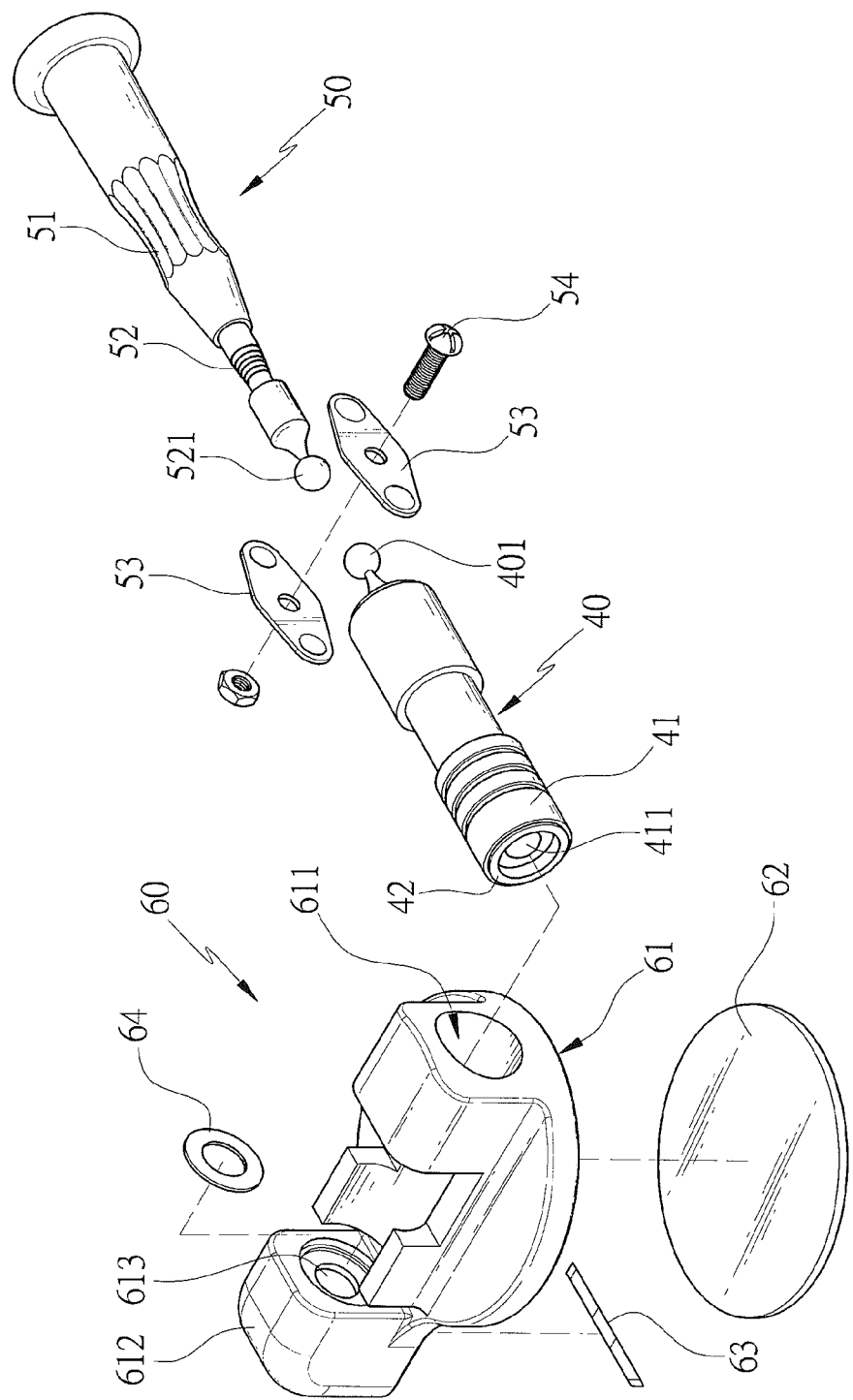
FIG. 4 is a perspective view showing the exploded components of an illumination tool according to a preferred embodiment of the present invention.
Figure 5:
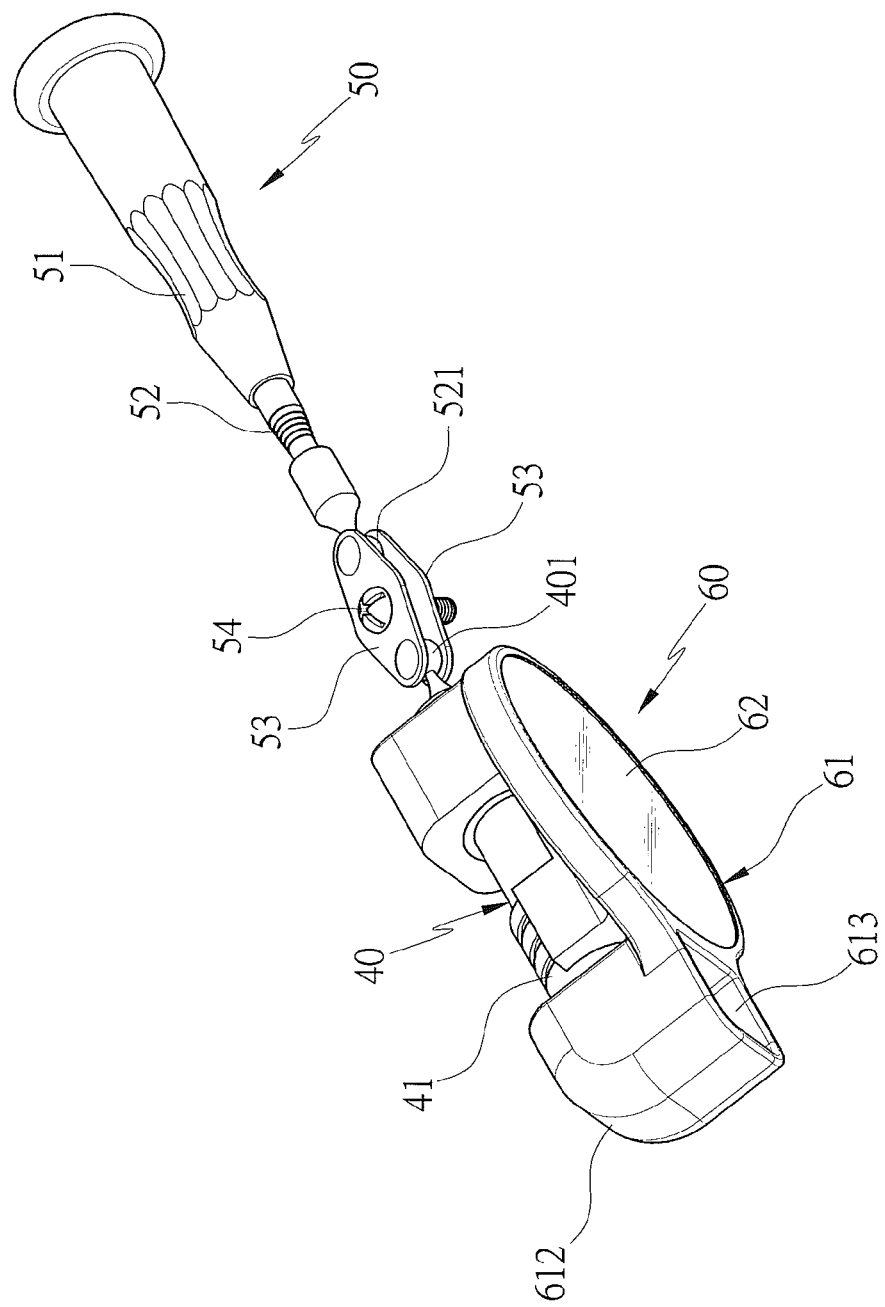
FIG. 5 is a perspective view showing the assembly of the illumination tool according to the preferred embodiment of the present invention.
Figure 6:
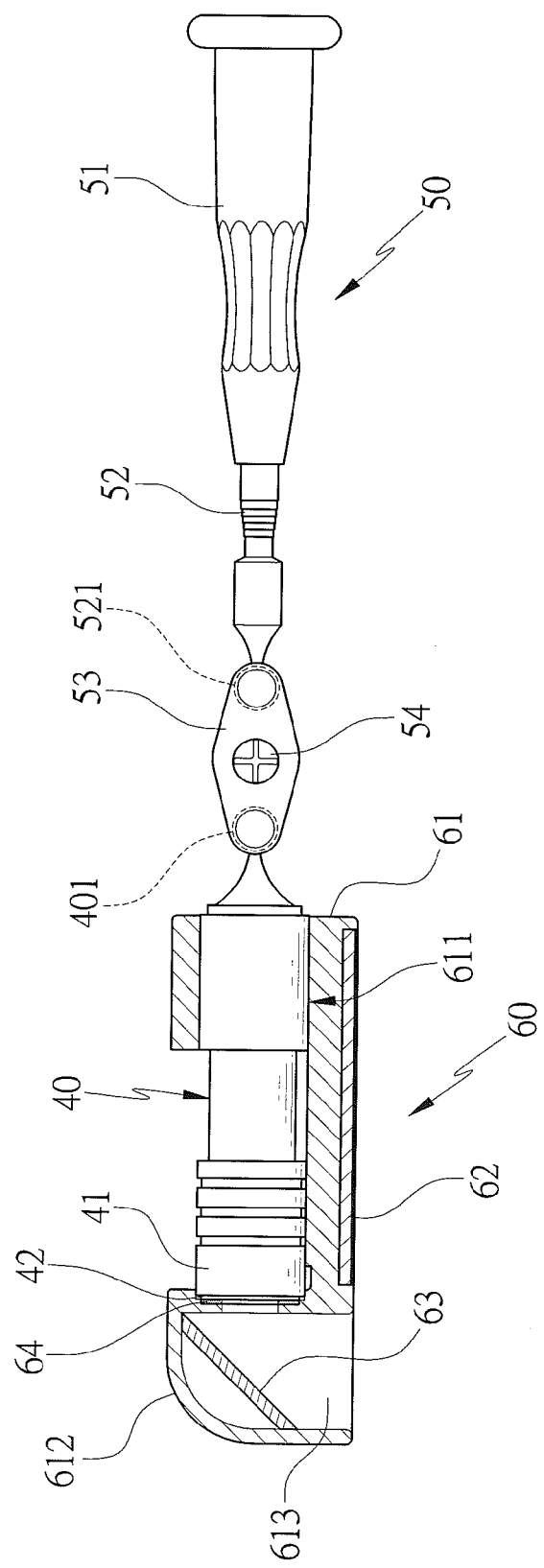
FIG. 6 is a cross sectional view the assembly of a part of the illumination tool according to the preferred embodiment of the present invention.

With reference to FIGS. 4 to 6, an illumination tool according to a preferred embodiment of the present invention comprises: a body 40, an extension assembly 50, and a mirror assembly 60.

The body 40 includes an accommodation mount 41 disposed on a front end thereof. The accommodation mount 41 has a light emitting element 411 housed therein and facing a first direction, a battery, and a power switch. The light emitting element 411 emits lights to the first direction, and the power switch is moved forward or backward to power on or off the light emitting element 411 of the accommodation mount 41. Since powering on/off of the light emitting element 411 of the accommodation mount 41 is a well-known art, further remarks are omitted. A front edge of the accommodation mount 41 is in connection with a magnetic sleeve 42 to magnetically attract a metal object. A rear end of the body 40 couples with the extension assembly 50, and between the extension assembly 50 and the body 40 is defined a rotation structure to extend or rotate the body 40. In this embodiment, the extension assembly 50 includes a hollow grip 51 and includes an expandable stem 52 disposed in the hollow grip 51. The rotation structure includes a first spherical rotating portion 401 formed on the rear end of the body 40, a second spherical rotating portion 521 formed on a front end of the expandable stem 52 of the extension assembly 50, and two clamping pieces 53 rotatably connected with the first spherical rotating portion 401 of the body 40 and the second spherical rotating portion 521 of the expandable stem 52. Each clamping piece 53 has two fixing grooves, and each fixing groove is defined on each of two ends of each clamping piece 53 to accommodate the first spherical rotating portion 401 of the body 40 or the second spherical rotating portion 521 of the expandable stem 52. A connecting bolt 54 inserts through and screws with the two clamping piece 53. The first spherical rotating portion 401 of the body 40 and the second spherical rotating portion 521 of the expandable stem 52 rotate along the two fixing grooves of each clamping piece 53. The body 40 adjustably extends forward or rotates to a desired angle by using the expandable stem 52 of the extension assembly 50 and the rotation structure, thus illuminating the target object.

The mirror assembly 60 includes a holder 61 facing a second direction, a first mirror 62 mounted on a first side surface of the holder 61 and facing the second direction, and a fitting portion 611 arranged on a second side surface of the holder 61 and facing the first direction to fit with the body 40. The holder 61 has a protrusion 612 extending outwardly from a front end of the second side surface thereof opposite to the fitting portion 611, and the protrusion 612 has an L-shaped channel 613 defined therein. A first end of the channel 613 corresponds to the accommodation mount 41 of the body 40 in the first direction. The lights illuminate into the channel 613 from the light emitting element 411 in the first direction, and a second end of the channel 613 curvedly extends to a front end of the first side surface of the holder 61 and faces the second direction with the first mirror 62. Furthermore, the channel 613 has a second mirror 63 fixed on a bending portion thereof to reflect the lights out of the second end of the channel 613 in the second direction from the light emitting element 411 in the first direction.

In this embodiment, an angle between the second mirror 63 and the first direction is 45 degrees. The channel 613 also has a magnetic attraction ring 64 mounted on an opening of the first end thereof, and the fitting portion 611 of the holder 61 fits with the body 40 in the first direction. Hence, the magnetic sleeve 42 of the accommodation mount 41 magnetically attracts the magnetic attraction ring 64 to fit the holder 61 with the body 40.

Figure 7:
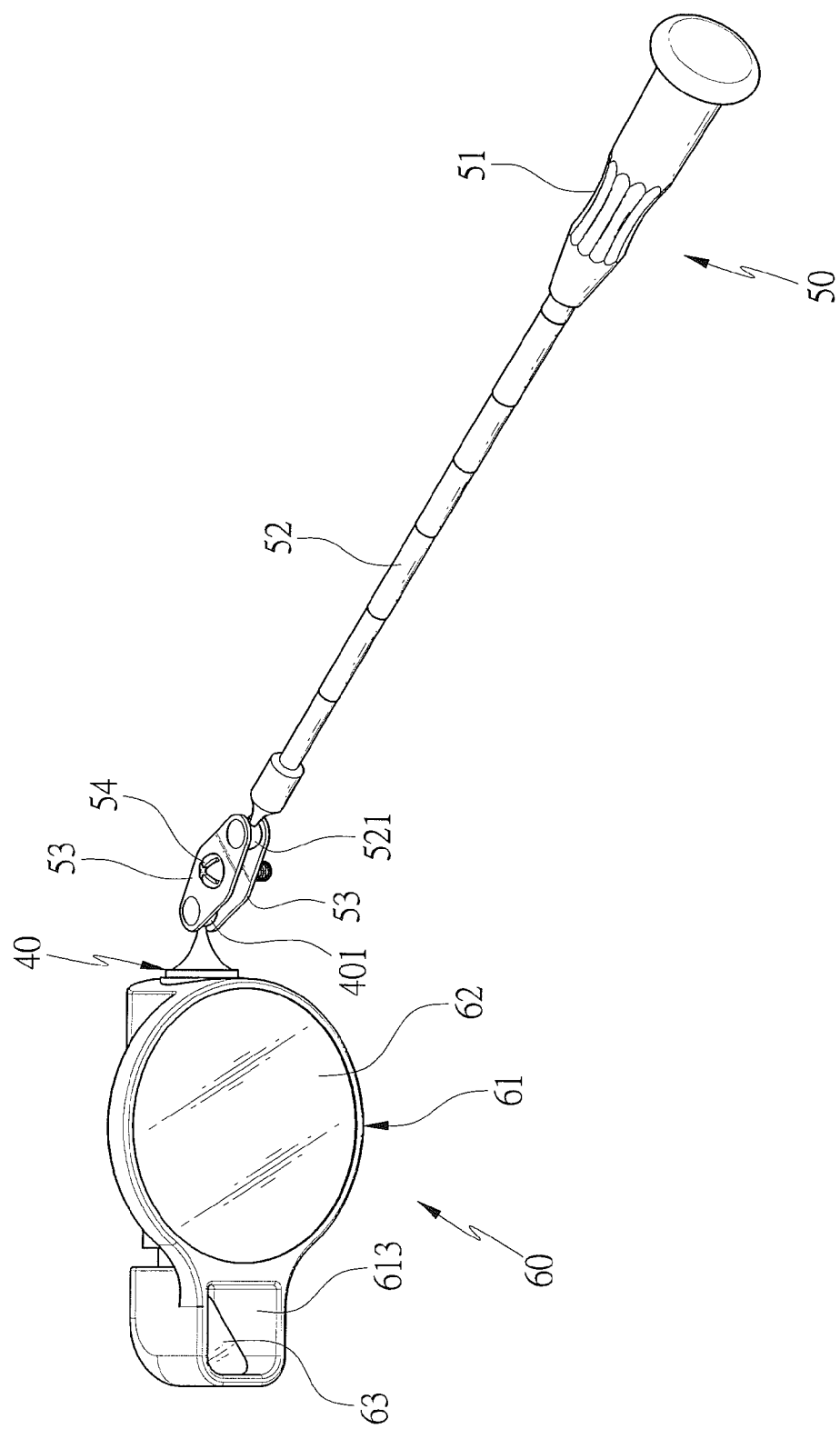
FIG. 7 is a perspective view showing the operation of the illumination tool according to the preferred embodiment of the present invention.
Figure 8:
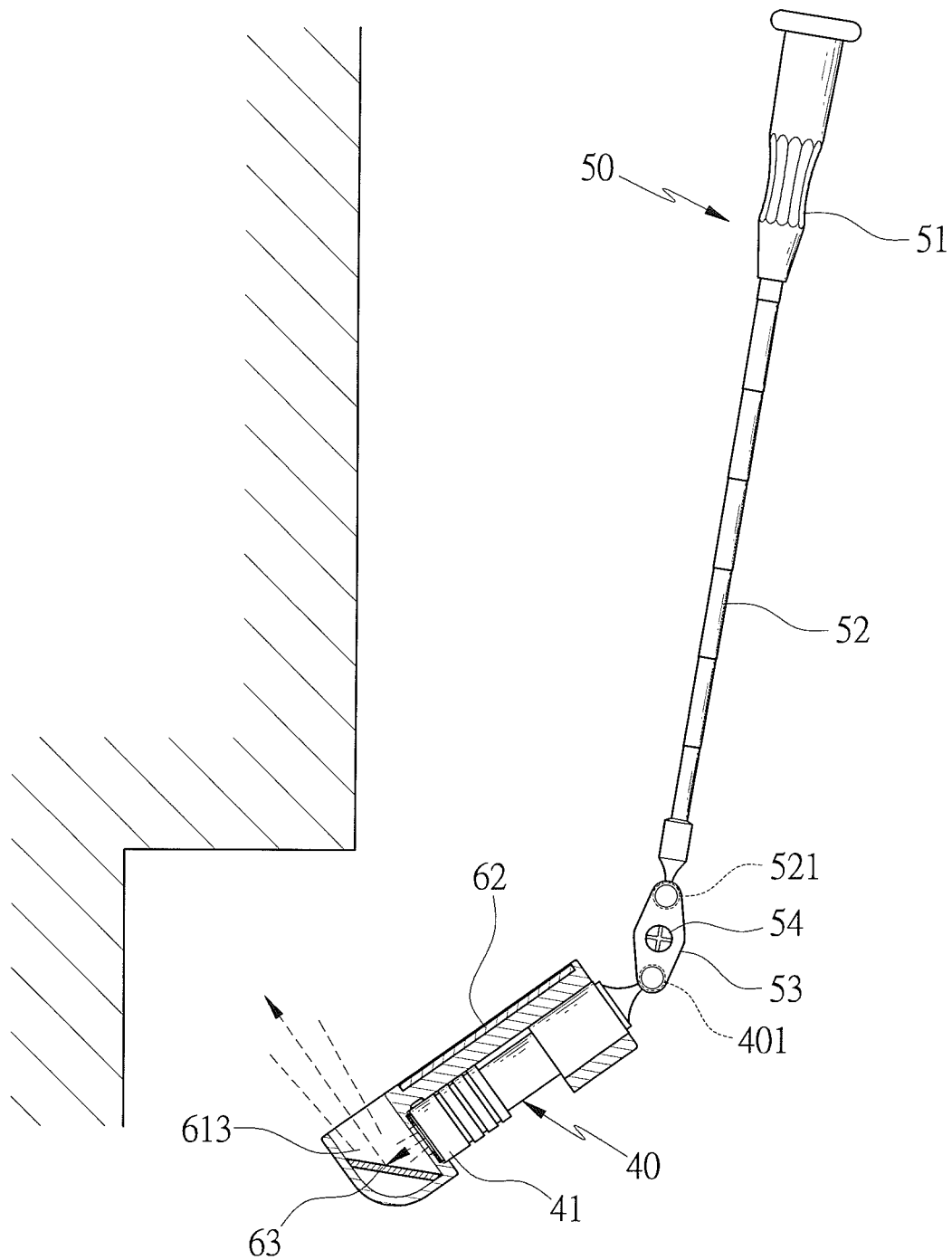
FIG. 8 is a cross sectional view showing the operation of the illumination tool according to the preferred embodiment of the present invention.

Referring to FIGS. 7 and 8, in operation, the expandable stem 52 of the extension assembly 50 extends outwardly. The body 40 and the mirror assembly 60 move close to the target object. An angle between the body 40 and the mirror assembly 60 is adjustable by ways of the rotation structure to rotate the first mirror 62 of the mirror assembly 60 to face the target object, and the second mirror 63 reflects the lights out of the second end of the channel 613 in the second direction from the light emitting element 411 via the channel 613. Thereafter, the target object is visible clearly by the first mirror 62. Accordingly, the connection structure between the body 40 and the extension assembly 50 allows adjusting an angle between the body 40 and the first mirror 62. The lights illuminate the target objects from the body 40 via the first mirror 62 of the mirror assembly 60, the second mirror 63 of the mirror assembly 60 reflects the lights to the target object in the second direction from the light emitting element 411, and the lights illuminate the target object in the second direction from the body 40. Preferably, the body 40 does not shield the first mirror 62 when viewing the target object.

Figure 9:
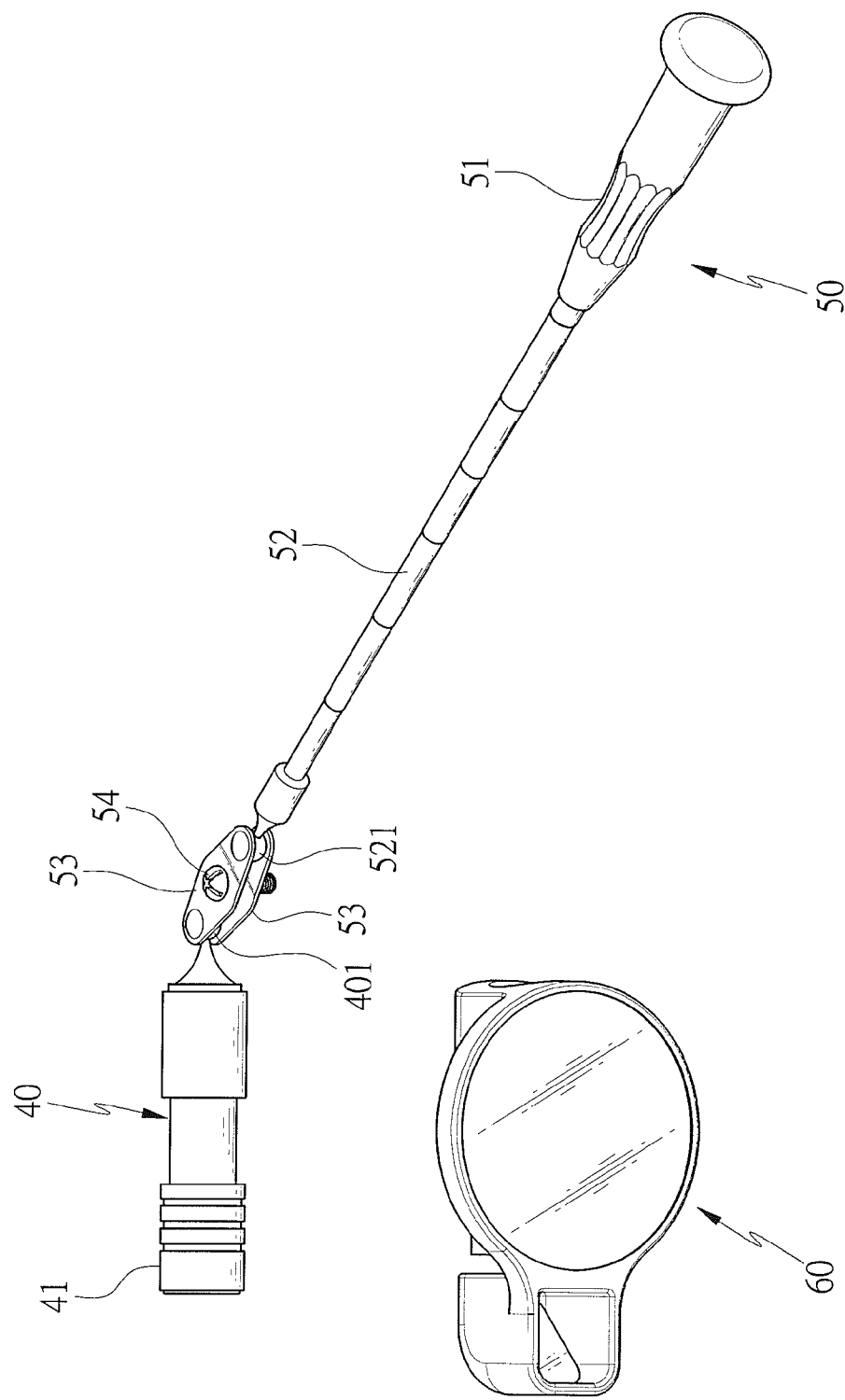
FIGS. 9 and 10 are other perspective views showing the operation of the illumination tool according to the preferred embodiment of the present invention.
Figure 10:
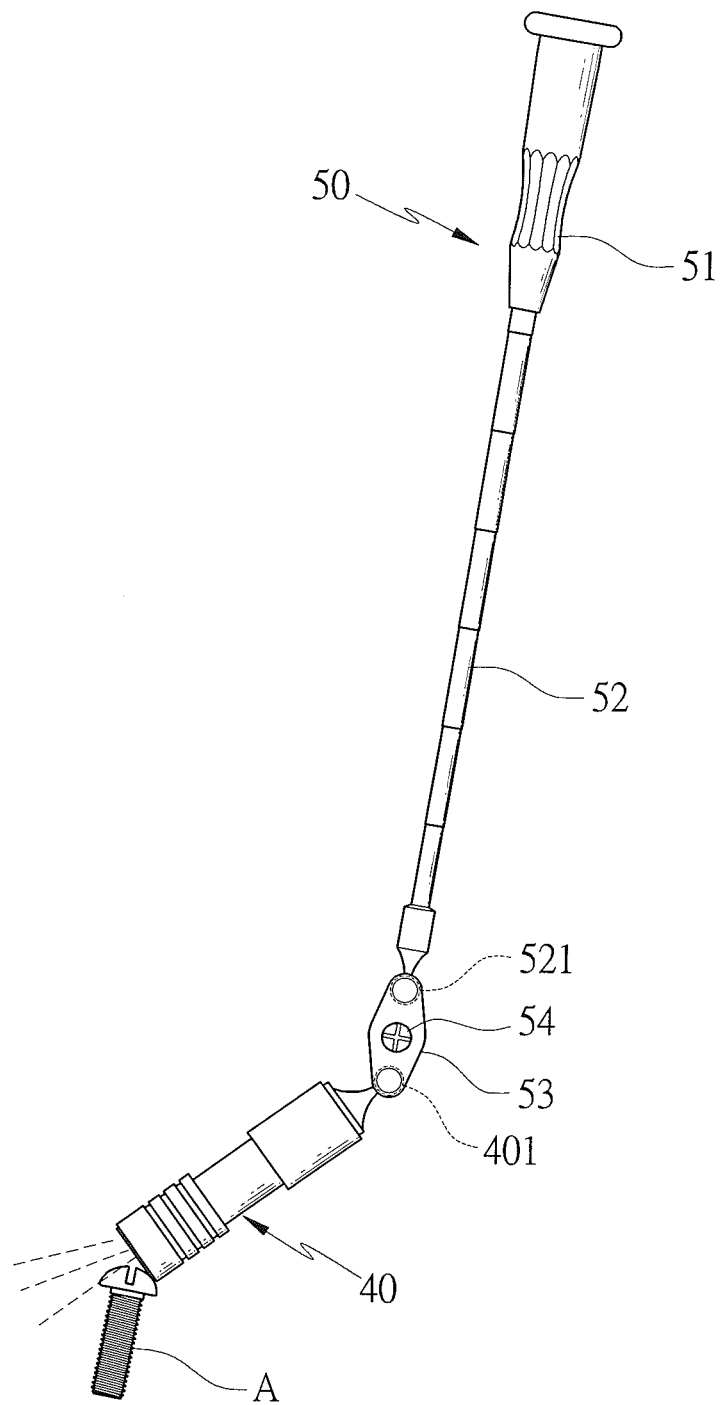

As shown in FIGS. 9 and 10, the mirror assembly 60 is removed, the expandable stem 52 of the extension assembly 50 is extended, and the body 40 is rotated to the desired angle by using the rotation structure between the body 40 and the expandable stem 52. Hence, the lights illuminate the metal object A, and the magnetic sleeve 42 magnetically attracts the metal object A in a long distance or in a limited space.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. An illumination tool comprising:
a body including an accommodation mount disposed on a front end thereof, with the accommodation mount having a light emitting element housed therein and facing a first direction, the body also including a magnetic sleeve for magnetically attracting a metal object;
an extension assembly coupling with a rear end of the body, and between the extension assembly and the body being defined a rotation structure; and
a mirror assembly including a holder facing a second direction, a first mirror mounted on a first side surface of the holder and facing the second direction, and a fitting portion arranged on a second side surface of the holder and facing the first direction, with the body fit into the fitting portion, with the second side surface being opposite to the first side surface, with the second direction not being parallel to the first direction;
with the holder having an L-shaped channel defined therein extending in the first direction aligned with the light emitting element of the body fit in the fitting portion and then extending in the second direction spaced from the first mirror, wherein a first end of the L-shaped channel corresponds to the accommodation mount of the body, wherein light illuminates into the L-shaped channel from the first direction, wherein a second end of the L-shaped channel curvedly extends to the second direction, wherein the L-shaped channel has a second mirror fixed on a bending portion thereof to reflect the light out of the second end of the channel in the second direction from the light emitting element, and wherein the first and second side surfaces of the holder being intermediate the first mirror and the light emitting element and the first end of the L-shaped channel.

2. The illumination tool as claimed in claim 1, wherein the extension assembly includes a hollow grip and includes an expandable stem disposed in the hollow grip.

3. The illumination tool as claimed in claim 2, wherein the rotation structure includes a first spherical rotating portion formed on the rear end of the body, a second spherical rotating portion formed on a front end of the expandable stem of the extension assembly, and two clamping pieces rotatably connected with the first spherical rotating portion of the body and the second spherical rotating portion of the expandable stem, wherein each clamping piece has two fixing grooves, wherein each fixing groove is defined on each of two ends of each clamping piece to accommodate the first spherical rotating portion of the body or the second spherical rotating portion of the expandable stem, and wherein a connecting bolt inserts through and screws with the two clamping piece.

4. The illumination tool as claimed in claim 1, wherein a front edge of the accommodation mount of the body is in connection with the magnetic sleeve.

5. The illumination tool as claimed in claim 1, wherein the holder of the mirror assembly has a protrusion extending outwardly from a front end of the second side surface thereof opposite to the fitting portion, and wherein the protrusion has the L-shaped channel defined therein.

6. The illumination tool as claimed in claim 1, wherein an angle between the second minor of the mirror assembly and the first direction is 45 degrees.

7. The illumination tool as claimed in claim 1, wherein the L-shaped channel of the holder of the mirror assembly also has a magnetic attraction ring mounted on an opening of the first end thereof.

8. The illumination tool as claimed in claim 1 wherein the first direction is perpendicular to the second direction.

* * * * *